(12) United States Patent
Cassano (10) Patent No.: US 11,577,094 B2
(45) Date of Patent: Feb. 14, 2023

(54) SYSTEMS AND METHODS OF LIGHT THERAPY FOR SEXUAL DYSFUNCTION

(71) Applicant: The General Hospital Corporation, Boston, MA (US)

(72) Inventor: Paolo Cassano, Lexington, MA (US)

(73) Assignee: The General Hospital Corporation, Boston, MA (US)

(*) Notice: Subject to any disclaimer, the term of this patent is extended or adjusted under 35 U.S.C. 154(b) by 66 days.

(21) Appl. No.: 16/500,775

(22) PCT Filed: Apr. 9, 2018

(86) PCT No.: PCT/US2018/026657
§ 371 (c)(1),
(2) Date: Oct. 3, 2019

(87) PCT Pub. No.: WO2018/191137
PCT Pub. Date: Oct. 18, 2018

(65) Prior Publication Data
US 2020/0086138 A1 Mar. 19, 2020

Related U.S. Application Data

(60) Provisional application No. 62/483,632, filed on Apr. 10, 2017.

(51) Int. Cl.
*A61N 5/06* (2006.01)
*A61N 5/067* (2006.01)

(52) U.S. Cl.
CPC ............ *A61N 5/0622* (2013.01); *A61N 5/067* (2021.08); *A61N 2005/0652* (2013.01); *A61N 2005/0659* (2013.01)

(58) Field of Classification Search
CPC ...... A61N 5/06; A61N 5/0618; A61N 5/0613; A61B 18/18; A61B 18/20; A61M 21/02
See application file for complete search history.

(56) References Cited

U.S. PATENT DOCUMENTS 9,149,256 B2 10/2015 Jeong
2011/0022130 A1 1/2011 Dimauro
(Continued)

FOREIGN PATENT DOCUMENTS

WO 2017197411 11/2017
WO WO-2017197411 A1 * 11/2017 ........... A61N 5/0618

OTHER PUBLICATIONS

"Sexual Problems in Men | Erectile Dysfunction." MedlinePlus, U.S. National Library of Medicine, Aug. 24, 2016, https://medlineplus.gov/sexualproblemsinmen.html. (Year: 2016).*
(Continued)

*Primary Examiner* — William J Levicky
*Assistant Examiner* — Michael A Rizzuto
(74) *Attorney, Agent, or Firm* — Quarles & Brady LLP (57) ABSTRACT

Systems and methods for treating sexual dysfunction using transcranial photobiomodulation (t-PBM) with near infrared light (NIR) are provided. In particular, a device configured for treating a disorder of a subject, the device can have a power source and a light source configured to receive power from the power source to cause the light source to emit near infrared light, wherein the near-infrared light has a wavelength of 600 nm to 1400 nm. The device has a processor and a housing configured to position the light source to deliver the near infrared light to a region of interest of the subject via transcranial photobiomodulation in a dosimetry and duration sufficient to treat the disorder.

16 Claims, 5 Drawing Sheets

(56) References Cited

U.S. PATENT DOCUMENTS

| | | | | |
|---|---|---|---|---|
| 2011/0040356 A1* | 2/2011 | Schiffer | ............... | A61M 21/02 |
| | | | | 607/88 |
| 2011/0319878 A1* | 12/2011 | DiMauro | ............. | A61N 5/0618 |
| | | | | 606/14 |
| 2012/0253429 A1 | 10/2012 | Schiffer | | |
| 2013/0138182 A1* | 5/2013 | Nissila | ................ | A61N 5/0618 |
| | | | | 607/88 |
| 2014/0358199 A1 | 12/2014 | Lim | | |
| 2016/0235980 A1* | 8/2016 | Berman | .............. | A61B 5/0006 |

OTHER PUBLICATIONS

Cassano, P., et al. (2015). Near-infrared transcranial radiation for major depressive disorder: proof of concept study. Psychiatry journal, 2015.

International Searching Authority, International Search Report and Written Opinion for application PCT/US2018/026657, dated Jun. 25, 2018.

\* cited by examiner

FIG. 1

```
┌─────────────────────────┐
│  Position Light Source to│  200
│ Deliver near infrared light to
│    region of interest    │
└─────────────────────────┘
            │
            ▼
┌─────────────────────────┐
│   Configure Operation of │  201
│    Device to Deliver     │
│  Therapeutically-Effective│
│           Dose           │
└─────────────────────────┘
            │
            ▼
┌─────────────────────────┐
│  Deliver Therapeutically-│  202
│ Effective Dose of light to│
│         subject          │
└─────────────────────────┘
```

SYSTEMS AND METHODS OF LIGHT THERAPY FOR SEXUAL DYSFUNCTION

CROSS-REFERENCE TO RELATED APPLICATION(S)

This application is a U.S. National Stage of PCT Application No. PCT/US2018/026657 filed on Apr. 9, 2018 which is based upon and claims the benefit of priority from U.S. Patent Application Ser. No. 62/483,632, filed on Apr. 10, 2017, the entire disclosure of which is incorporated herein by reference.

BACKGROUND

The present invention relates generally to methods and systems for treating sexual dysfunction and, more particularly, to systems and methods for using photobiomodulation (t-PBM) with near infrared light (NIR) to treat sexual dysfunction.

Sexual dysfunction is common and it affects 43% of women and 31% of men in US. Sexual dysfunction might involve decreased sexual desire (libido), insufficient sexual arousal—such as incomplete engorgement of the penis or of the clitoris or lack of vaginal lubrication-, and delayed or absent sexual orgasm (anorgasmia), or a combination of the above.

The causes for sexual dysfunction are disparate and include psychiatric, neurological, endocrine, cardiovascular and pelvic conditions, as well as commonly prescribed medications. While any of the listed causes is sufficient to produce sexual dysfunction, a multifactorial causation is rather the norm than the exception. Considering major depressive disorder (MDD)—a common cause of sexual dysfunction with up to 50% of untreated depressed patients suffering from sexual dysfunction, MDD is frequently comorbid with other physical illnesses, and its prevalence is twice as high in patients who also suffer from at least two other chronic medical conditions. The same patients are also likely to receive medications for MDD or for other medical conditions, or to take supplements or medications for wellness, such as oral contraceptives. It is then apparent that multiple causes of sexual dysfunction can coexist, such as psychiatric disorders, other medical conditions and pharmacotherapy, whether medications are prescribed for the treatment of the same medical disorders or taken for wellness. The sample of patients with sexual dysfunction discussed below exemplifies the multifactorial nature of causality of sexual dysfunction.

Multiple treatments exist for women and men with sexual dysfunction; however, as patients increasingly turn to alternative medicine and to non-pharmacological interventions to treat their ailments, scientifically sound alternatives to the current medications for the treatment of sexual dysfunction are needed.

Accordingly, at least one of the objects of the invention is to address such deficiencies and issues.

SUMMARY OF THE DISCLOSURE

The present disclosure overcomes the aforementioned drawbacks by providing systems and methods of photobiomodulation (PBM) with near infrared light (NIR), including transcranial PBM (t-PBM). Using the systems and methods herein, the NIR is absorbed by mitochondria to increase cellular energy metabolism. Non-limiting beneficial effects of t-PBM in accordance with the present disclosure include pro-cognitive, antidepressant, and anxiolytic effects. The systems and methods provided herein, however, are particularly designed to implement PBM to treat sexual dysfunction and have been demonstrated as effective in a cohort of depressed patients with medical and psychiatric comorbidity and concomitant pharmacological therapies.

In accordance with one aspect of the disclosure, a device is configured for treating a sexual dysfunction of a subject. The devices includes a power source, a light source configured to receive power from the power source to cause the light source to emit near-infrared light, wherein the near-infrared light has a wavelength of 600 nm to 1400 nm, and a processor. The device also includes a housing configured to position the light source to deliver the near infrared light to a region of interest of the subject via transcranial photobiomodulation in a dosimetry and duration sufficient to treat the sexual dysfunction of the subject.

In accordance with another aspect of the disclosure, a device configured for treating a disorder of a subject is provided. The device comprises a power source, a light source configured to receive power from the power source to cause the light source to emit near-infrared light. The near-infrared light has a wavelength of 600 nm to 1400 nm. The device further comprises a processor and a housing configured to position the light source to deliver the near infrared light to a region of interest of the subject via transcranial photobiomodulation in a dosimetry and duration sufficient to treat the disorder.

In some aspects, the disorder is sexual dysfunction. In some aspects, the disorder is at least one of impaired libido, impaired sexual arousal, delayed or absent orgasm. The near-infrared light can have one of a wavelength of about 825 nm, a wavelength of about 850 nm, or a wavelength of about 808 nm to about 830 nm. The duration of delivery of near infrared light can be about 1 minute to about 120 minutes per day. The near infrared light can be delivered at a wavelength of 830 nm at an average irradiance up to 36.2 $mW/cm^2$ and a fluence over 30 min up to 65.2 $J/cm^2$, with a treatment window of 28.7 $cm^2$.

In accordance with another aspect of the disclosure, a method of controlling a device configured for treating a disorder of a subject is provided. The method comprising: providing power to a device having a light source to cause the light source to emit near infrared light to a region of interest of the subject, the near-infrared light has a wavelength of 600 nm to 1400 nm. The method further comprising delivering near infrared light to a region of interest of the subject via transcranial photobiomodulation in a dosimetry and duration sufficient to treat the disorder.

In some aspects, the disorder is sexual dysfunction. In some aspects, the disorder is at least one of impaired libido, impaired sexual arousal, delayed or absent orgasm. The near-infrared light can have one of a wavelength of about 825 nm, a wavelength of about 850 nm, or a wavelength of about 808 nm to about 830 nm. The duration of delivery of near infrared light can be about 1 minute to about 120 minutes per day. The near infrared light can be delivered at a wavelength of 830 nm at an average irradiance up to 36.2 $mW/cm^2$ and a fluence over 30 min up to 65.2 $J/cm^2$, with a treatment window of 28.7 $cm^2$.

BRIEF DESCRIPTION OF THE DRAWINGS

Further objects, features and advantages of the invention will become apparent from the following detailed description taken in conjunction with the accompanying figures showing illustrative embodiments of the invention, in which.

The following Detailed Description, given by way of example, but not intended to limit the invention to specific embodiments described, may be understood in conjunction with the accompanying figures, incorporated herein by reference.

DETAILED DESCRIPTION

As used herein, the terms "treat," "treating," "treatment," and the like refer to reducing or ameliorating disorders, such as sexual dysfunction and/or a brain disorder and/or symptoms associated therewith. It will be appreciated that, although not precluded, treating a brain disorder or condition does not require that the disorder, condition, or symptoms associated therewith be completely eliminated.

Unless specifically stated or clear from context, as used herein, the term "about" is understood as within a range of normal tolerance in the art, for example within 2 standard deviations of the mean. "About" is understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used herein, the term "effective," means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "transcranial photobiomodulation", means the use of several therapeutic techniques that employ infrared light, low-level laser, and/or LED light to treat a disorder across or through the skull.

Figure 1:
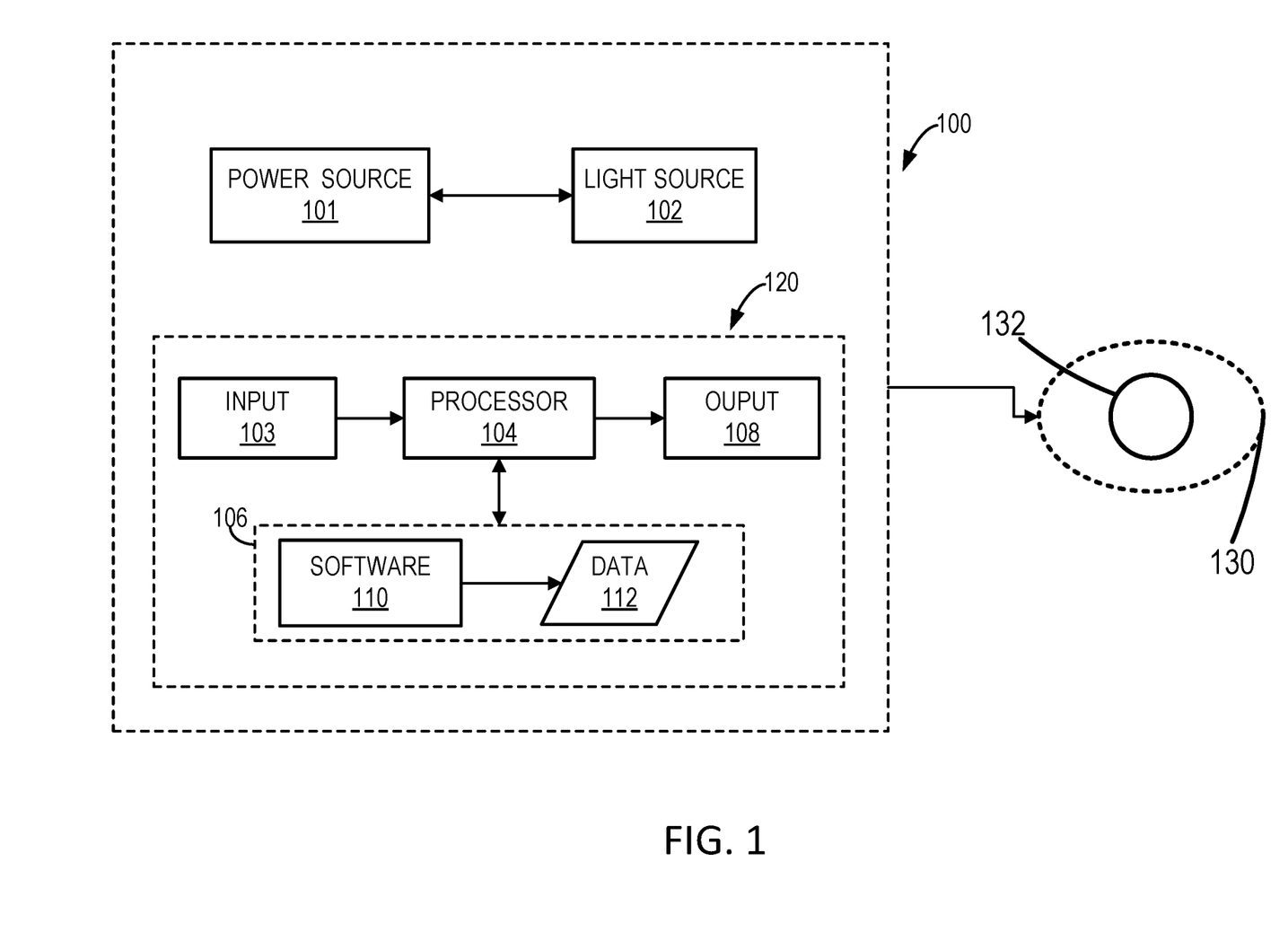
FIG. 1 is a schematic diagram depicting a device for transcranial photobiomodulation in accordance with the present disclosure.

FIG. 1 shows an exemplary device 100 having a power source 101 and a light source 102, the power source 101 configured to provide power to the light source 102. At least one light source 102 is implemented in the system, accordingly, a number of light sources 102 can be implemented in the device 100. The light source 102 may be a light-emitting diode (LED) source that may include a single LED or an array of LEDs. In one non-limiting example, the light source 102 may emit NIR light to a region of interest 132 of a subject 130 at a predefined wavelength. In a non-limiting example, the light source 102 may emit NIR at a wavelength of 830 nanometers (nm), with an average irradiance up to 36.2 mW/cm$^2$ and fluence over 30 min up to 65.2 J/cm$^2$, with a treatment window of 28.7 cm$^2$ per system 102. In some embodiments, two devices 100 may be implemented, the devices 100 can be positioned to provide NIR to be administered to the forehead bilaterally, directed to the region of interest, which may be the F3 and F4 sites—per the EEG placement map—for the dorsolateral prefrontal cortex (dlPFC). As additional or alternative, non-limiting examples, other spots on the forehead, such as Fp1 or Fp2 or others on the forehead or other areas may be utilized.

A block diagram of an example of a controller 120 that can be integrated in the device 100 to perform the methods described in the present disclosure is shown. The controller 120 is generally implemented with a hardware processor 104 and a memory 106.

The controller 120 generally includes an input 103, at least one hardware processor 104, a memory 106, and an output 108. The controller 120 can also include any suitable device for reading computer-readable storage media. The controller 120 may be implemented, in some examples, by a workstation, a notebook computer, a tablet device, a mobile device, a multimedia device, a network server, a mainframe, one or more controllers, one or more microcontrollers, or any other general-purpose or application-specific computing device. The controller 120 may operate autonomously or semi-autonomously, or may read executable software instructions from the memory 106 or a computer-readable medium (e.g., a hard drive, a CD-ROM, flash memory), or may receive instructions via the input 103 from a user, or any another source logically connected to a computer or device, such as another networked computer or server.

In general, the controller 120 is programmed or otherwise configured to implement the methods and algorithms described below. For instance, the controller 120 is programmed to provide power to the light source 102 via the power source 101 to emit the near-infrared light, in accordance with any of the dosimetries, durations, or pulse sequences described herein. In one non-limiting example, LED and laser devices may be used. Additionally or alternatively, wavelengths of 600-1400 nm may be used. A given does may be delivered as continuous and/or pulse light CW or PW 1-300 Hz (mostly 10 Hz, 20 Hz, 30 Hz, 40 Hz). Average irradiance may be, for example, 10-750 mW/cm$^2$. Average fluence, for example, may be 10-160 J/cm$^2$. As another example, a treatment duration may extend from 1-120 min per day.

The input 103 may take any suitable shape or form, as desired, for operation of the controller 120, including the ability for selecting, entering, or otherwise specifying parameters consistent with performing tasks, processing data, or operating the controller 120. In some aspects, the input 103 may be configured to receive data, such as data acquired through a user interface. Such data may be processed as described above to determine the correct dosimetry, duration, pulse sequence, or any other testing variable.

The memory 106 may contain software 110 and data 112, such as data acquired with a user interface, and may be configured for storage and retrieval of processed information, instructions, and data to be processed by the one or more hardware processors 104. In some aspects, the software 110 may contain instructions directed to emit the near-infrared light at various organs and/or systems within the head or other parts of the subject, as desired.

Figure 2:
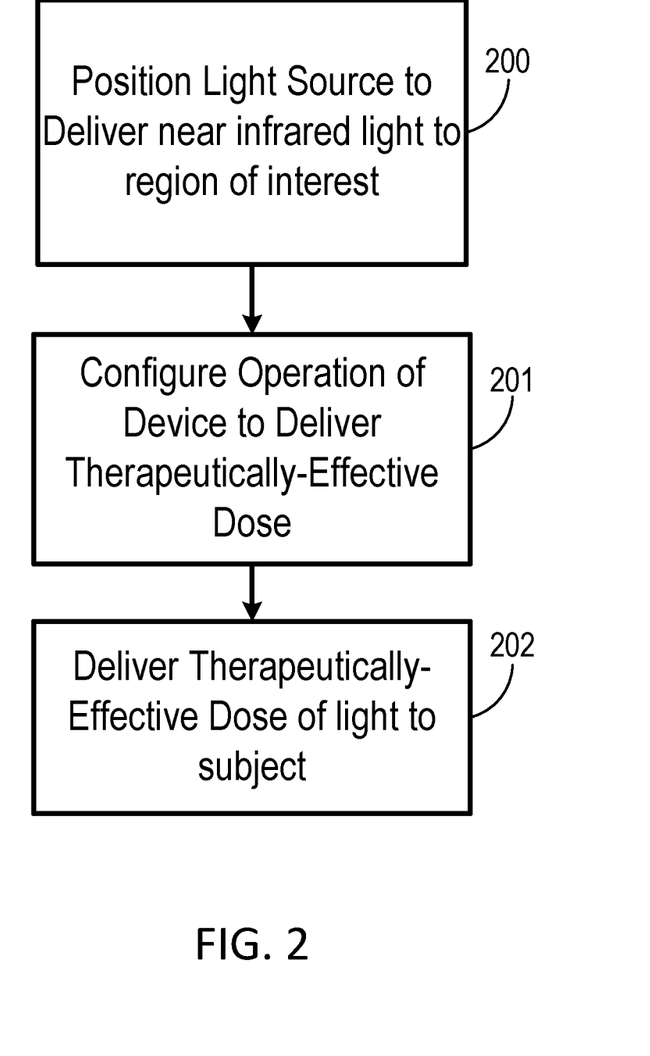
FIG. 2 is a flowchart which provides non-limiting examples of steps for a method for transcranial photobiomodulation using the system of FIG. 1.

FIG. 2 shows an exemplary method of the disclosure. The method can include step 200 positioning the light source, such as the light source 102, to deliver near infrared light to a region of interest, such as the region of interest 132 of the subject 130. Step 201 of the method can include controlling the device, such as the device 100, to select and/or otherwise configure the device to deliver a therapeutically-effective dose to treat the subject. The device 100 can have the light source 102 described above, and the power provided to the device 100 may be sufficient to cause the light source 102 to emit near infrared light to a region of interest 132 of the subject 130. One non-limiting example of a therapeutically-effective dose can be about 0.1-5 kJ per session or 2.4 kJ or 3.4 kJ per session. Sessions can be weekly, daily, or even several times a day such as twice daily, or variations between. Step 202 of the method may be delivering near infrared light to a region of interest 132 of the subject via transcranial photobiomodulation in a dosimetry and duration sufficient to treat the disorder.

In some configurations, the near-infrared light may have a wavelength of 600 nm to 1400 nm. More particularly, configuring or controlling the device may include causing the near-infrared light to have a wavelength of about 825 nm, a wavelength of about 850 nm, or a wavelength of about 808 nm to about 830 nm. Additionally, the configuring or controlling may include causing a processor of the device to control the light source to implement a duration of delivery of near infrared light of about 1 minute to about 120 minutes per day. In one non-limiting example, the device may be configured and/or controlled to deliver the near infrared light at a wavelength of 830 nm at an average irradiance up to 36.2 $mW/cm^2$ and a fluence over 30 min up to 65.2 $J/cm^2$, with a treatment window of 28.7 $cm^2$. In this way the therapeutically-effective dose may be effective to treat sexual dysfunction, which may include at least one of impaired libido, impaired sexual arousal, delayed or absent orgasm.

The following provides information about a study implementing and demonstrating non-limiting examples in accordance with the present disclosure.

Methods and Materials

Inclusion and Exclusion Criteria

Adult subjects (age 18-65 years) meeting the Diagnostic and Statistical Manual of Mental Disorders, fourth edition (DSM-IV) Structured Clinical Interview Disorders (SCID) criteria for MDD, with the degree of depression severity rated at least moderate (Hamilton Depression Rating Scale, $HAM-D_{17}$ total score ranging 14-24), were included in the study after providing written informed consent. During the current episode, subjects could have failed no more than one FDA-approved antidepressant medication (for at least 6 weeks) and no more than one course of structured psychotherapy for depression (for at least 8 weeks). Other exclusionary conditions included active substance use disorders (prior 6 months), lifetime psychotic episodes, bipolar disorder, active suicidal ideation and homicidal ideation, in addition to unstable medical illness and recent stroke (prior 3 months). Women of childbearing potential were required to use a birth-control method if sexually active; pregnancy and lactation were exclusionary. To allow maximum light penetration and to minimize potential risks of local tissue damage from the use of NIR, the following conditions were also exclusionary: 1. having a forehead skin condition; 2. taking a light-activated medication (prior 14 days); 3. having a head-implant.

Study Design and Treatment

Eligible subjects were randomized to an 8-week study with twice-weekly double-blind NIR t-PBM vs. sham therapy (16 sessions total). At each session, NIR or sham were administered to the forehead bilaterally, directed to the F3 and F4 sites—per the EEG placement map—for the dorsolateral prefrontal cortex (dlPFC). The study clinician had the option to adjust the duration of light exposure after reaching week 4 and week 6 (after 6 and 10 sessions respectively) from 20 minutes to 25 and 30 minutes respectively, based on tolerability and efficacy. The study devices employed an LED source emitting NIR at a wavelength of 830 nm, with an average irradiance up to 36.2 $mW/cm^2$ and fluence over 30 min up to 65.2 $J/cm^2$, with a treatment window of 28.7 $cm^2$ per each of the two devices. All but three subjects remained on stable antidepressant treatment during the trial; their data were censored after change in concomitant antidepressant therapies.

Randomization and Blinding

Two t-PBM device types were available for each modality (NIR and sham). The apparent behavior (i.e. all visible and audible indicators) of the devices was identical for both modalities. However, only NIR-mode t-PBM device produced the therapeutic NIR energy. NIR light is invisible and undetectable to patients and physicians. The study research assistant used permuted block randomization with varying block sizes to randomize subjects in 1:1 fashion to each pair of instruments as "A" and "B". Only the research assistant was able to identify each pair of instruments as "A" and "B". The investigators and the subjects remained blind to the subject assignment, since the label on each device was covered prior to treatment administration. The blinding codes of NIR and sham were in a sealed envelope at the study site, for each labeled pair of devices. Prior to this secondary paper, the blinding in ELATED-2 had already been tested, and there were no significant correlations between treatment assignment and the guess made by the subjects as to which treatment they were receiving.

Clinical Outcome Measures

The outcome measure for this secondary analysis of the ELATED-2 study was the overall sexual dysfunction, assessed by weekly and systematic self-reporting by the Systematic Assessment for Treatment-Emergent Effects—Specific Inquiry (SAFTEE-SI) scale (Levine and Schooler 1992). A checklist of fifty-five (55) adverse symptoms commonly or possibly experienced during treatment and categorized by severity as zero (0)—none, one (1)—mild, two (2)—moderate, three (3)—severe. From the SAFTEE scale, three items were identified as pertinent to the sexual dysfunction: item 36-loss of sexual interest, item 37-problems with sexual arousal (erection or lubrication), and item 38-delayed or absent orgasm. A composite score was generated by adding the rating for each of the three items—the SAFTEE sex total score (ranging 0-9) indicating the overall sexual dysfunction, the higher the score representing increased or worse dysfunction. No attributions were made as to whether the sexual dysfunction was influenced by the underling major depressive disorder, by concomitant medications, by comorbid illnesses or disorders or by other factors, including study participation and t-PBM. The instructions for self-rating were in fact generic: "below is a list of symptoms people sometimes have; please read each item; indicate how bothersome each symptom has been for you by circling the appropriate number to the right of the item".

Study Sample and Data Cleaning

Twenty-one (21) randomized subjects who received at least one t-PBM session were included in the original ELATED-2 sample. However, for this secondary analysis—on repeated measures of self-rated scales—the sample is limited to 20 subjects, since one subject in the original pool consistently skipped several answers on the scales for the duration of the study. This subject had received a diagnosis of attention-deficit disorder and reported significant difficulties concentrating while off stimulants. As briefly mentioned, three subjects were censored as part of the a-priori data cleaning process due to their starting new psychoactive treatments during the course of the study. All other available data were included, regardless of dropouts.

Analyses:

The prevalence of conditions and treatments commonly associated with sexual dysfunction using descriptive statistics. Unpaired Mann-Whitney (two-tailed) and Pearson's Chi-square test, respectively compared baseline characteristics for the NIR and sham groups, for continuous and nominal variables. A Mann-Whitney U test (two-tailed) was also chosen to compare the change in the total severity score for sexual dysfunction (SAFTEE sex total score) from baseline to endpoint—last evaluation carried forward-, across the two study groups. The following subsamples repeated the same analysis: in completers, in all women and in all men. For specific types of sexual dysfunction such as impaired libido, arousal, and orgasm, the change in severity score for each of the three SAFTEE items (36, 37, 38) was compared, in the whole sample and in completers (Mann-Whitney U test, two-tailed). The small sample size caused the use of non-parametric tests, and did not cover for the change in depression severity. As post-hoc analyses, to better discern whether the antidepressant effect was driving the effect on sexual functioning, Cohen's d effect size of t-PBM for the change of severity of sexual dysfunction and for the change in severity of depression (HAM-$D_{17}$ total score) was calculated. Second, the timing of significant changes in sexual dysfunction and in depression severity were assessed, since plotting of means suggested an early improvement of sexual functioning (last evaluation carried forward up to the specific time point and Mann-Whitney U test, two-tailed for the change from baseline). The analyses were repeated on the primary outcome, the overall change in sexual dysfunction, after removing two subjects with no assessments after baseline (n=18; Mann-Whitney U test, two-tailed). For all analyses, significance was set at $p \leq 0.05$.

Results

Etiology of Sexual Dysfunction and Baseline Characteristics

Per inclusion criteria, all subjects (n=20) had major depressive disorder, a common cause of sexual dysfunction. Of note, 45% and 25% of subjects in the same group were diagnosed with at least one or two additional psychiatric disorders, respectively; the most common being generalized anxiety disorder, post-traumatic stress disorder and social anxiety disorder. Non-psychiatric medical conditions affected nearly all subjects (approximately 85% of subjects); many of which are potentially implicated in sexual dysfunction. Endocrine conditions were among the most common (30%) and included thyroid and parathyroid diseases and thyroid hormone supplementation. Neurological conditions were equally common (30%) and included history of concussion, spinal cord injury and chronic pain syndromes. Cardiovascular diseases and metabolic syndrome (25%) included hypertension, hyperlipidemia and obesity. One case of pelvic disorder was due to hysterectomy. Nearly all subjects (80%) received pharmacological therapies. Some non-limiting examples of prescribed medications with sexual dysfunction described as a potential side effect include antidepressants or other psychiatric medications taken by 45% of the subjects; antiepileptic medications by 15%; α2-agonists, diuretics, statins or calcium channel blockers also by 15%. Other non-limiting examples of medications or other drugs with sexual dysfunction described as a potential side effect include one subject took narcotics and NSAIDS; oral contraceptive (or other means of contraception) were required for study entry of women of child-bearing age. See Table 1 for an overview on these medical conditions and treatments commonly affecting sexual functioning, and for their prevalence rates in our study sample. In sum, 90% of study subjects had at least one additional explanation—other than depression or other psychiatric diagnoses—for their sexual dysfunction.

TABLE 1

Prevalence of Conditions and Treatments Commonly Affecting Sexual Functioning (sample: n = 20)

| | |
|---|---|
| Neurological: | Concussion, spinal cord injury and chronic pain (n = 6) |
| | Antiepileptic drugs (n = 3) |
| | Narcotics and NSAIDS (n = 1) |
| Endocrine: | Thyroid disease and thyroid hormone supplementation and parathyroid disease (n = 6) |
| Cardiovascular & Metabolic Syndrome: | Obesity, hypertension and hyperlipidemia (n = 5) Alpha2-agonist, diuretics, statins or calcium channel blockers (n = 3) |
| Psychiatric: | Major Depressive Disorder (n = 20) |
| | Generalized Anxiety Disorder (n = 5) |
| | Post-Traumatic Stress Disorder (n = 5) |
| | Social Anxiety Disorder (n = 3) |
| | Antidepressants or other psychiatric medications (n = 9) |
| Pelvic disorders: | Hysterectomy (n = 1) |

There were no significant differences between the two groups at baseline in terms of demographic and clinical characteristics as well as concurrent antidepressant treatment, as will be discussed in more detail in the examples below. During the study, all subjects continued their baseline antidepressant treatment, if any, except one subject in the t-PBM NIR group, who discontinued her psychotherapy at baseline.

TABLE 2

Table 2: Demographic and Clinical Characteristics of the Sample:

| | Active (n = 9) | Sham (n = 11) | p value |
|---|---|---|---|
| Age | 47.3 ± 11.1 | 50.7 ± 13.3 | 0.361 |
| Gender (female) | 5 (56%) | 6 (55%) | 0.964 |
| Race | | | 0.36 |
| White | 8 (89%) | 10 (91%) | |
| Asian | 1 (11%) | 0 | |
| African American | 0 | 1 (9%) | |
| Ethnicity | | | |
| Not Hispanic or Latino | 8 (100%) | 11 (100%) | — |
| Using AD medication | 3 (33%) | 3 (27%) | 0.769 |
| SAFTEE Sex Total Score | 3.3 ± 1.9 | 4.2 ± 3.5 | 0.783 |
| HAM-D | 19.7 ± 1.9 | 20.2 ± 4.3 | 0.847 |
| CGI Severity of Depression | 4.4 ± 0.5 | 4.4 ± 0.5 | 0.916 |

The abbreviations used in Table 2 are as follows: AD: Antidepressant; HAM-D: Hamilton Depression Rating Scale (17 items); CGI-S: Clinical Global Impression Severity Scale.

Overall Sexual Dysfunction

Figure 3:
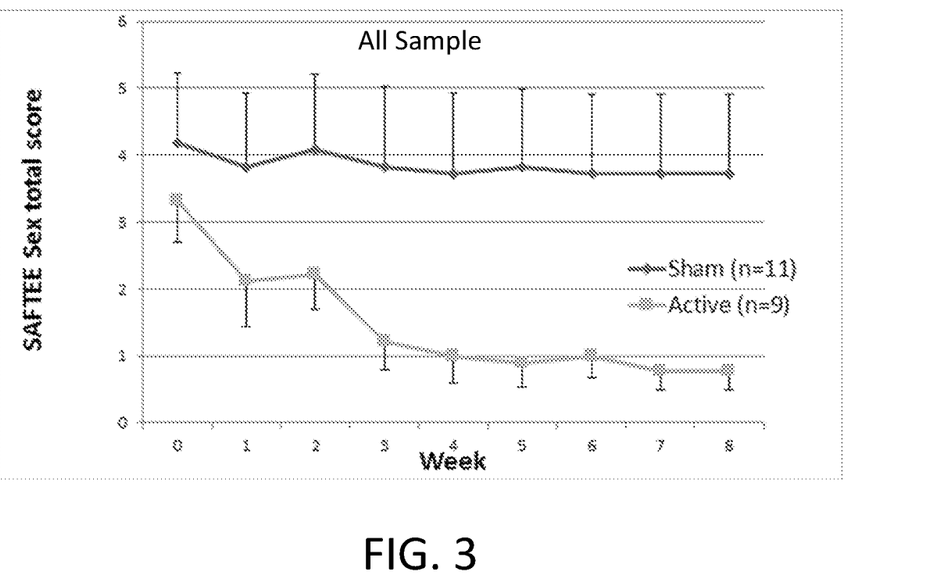
FIG. 3 is a graph of SAFTEE Sex Total Score over time showing the effects of t-PBM on sexual dysfunction on all samples.
Figure 4:
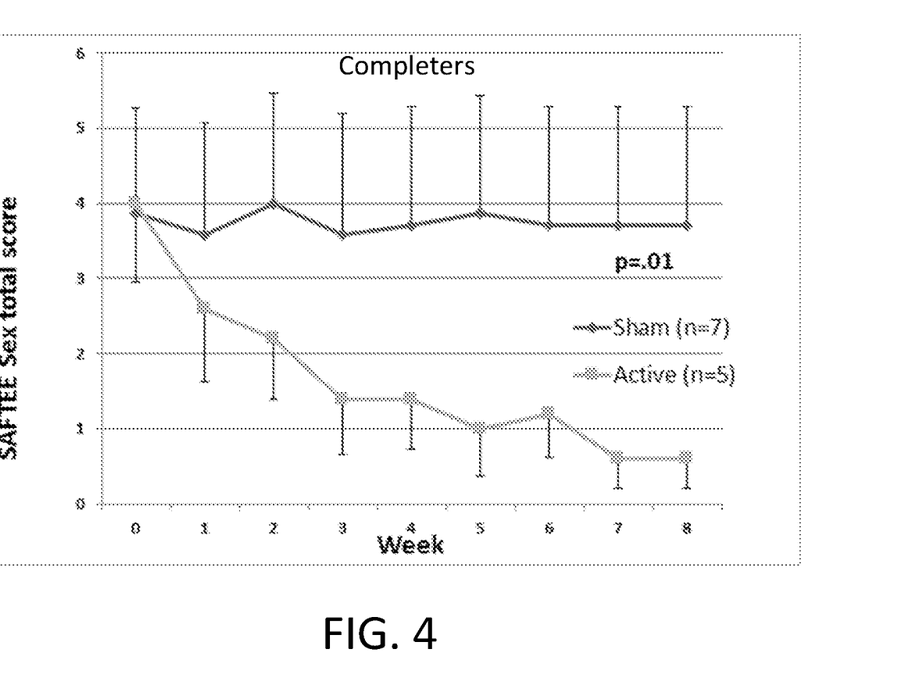
FIG. 4 is a graph of SAFTEE Sex Total Score over time showing the effects of t-PBM on sexual dysfunction on completers.
Figure 5:
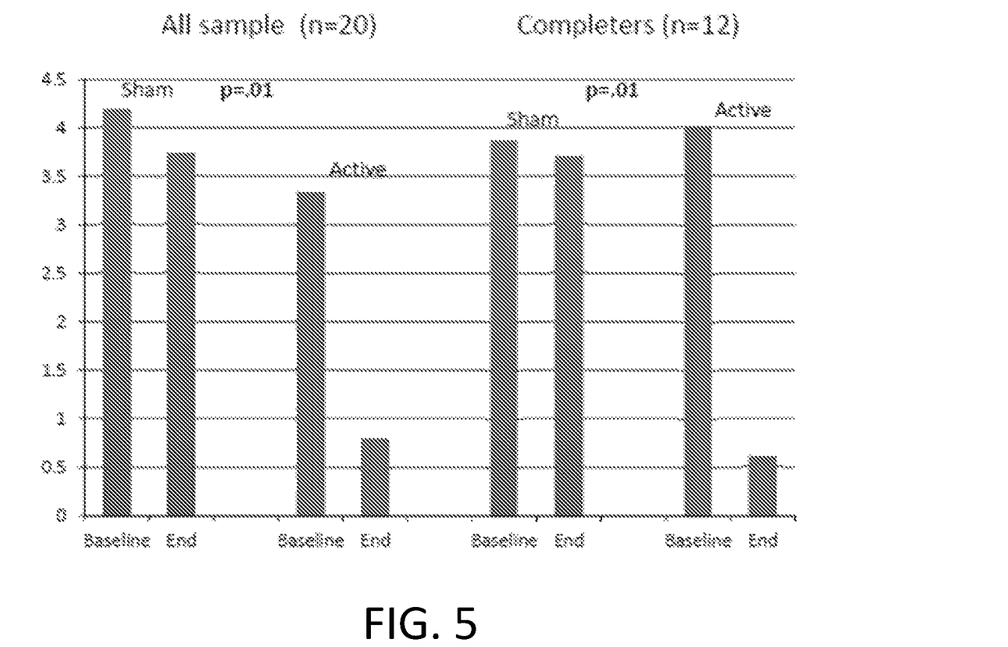
FIG. 5 is a chart of SAFTEE Sex Total Score pre-treatment and post treatment.
Figure 6:
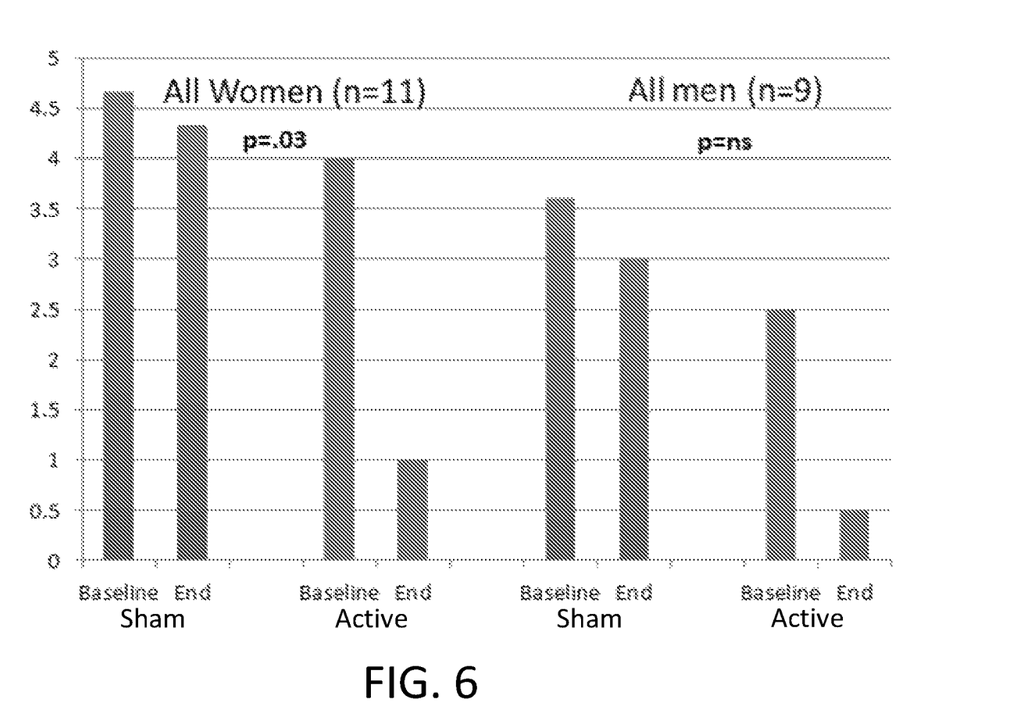
FIG. 6 is a chart of SAFTEE Sex Total Score pre-treatment and post treatment for all women and all men.

The mean change in SAFTEE sex total score in subjects receiving t-PBM in NIR-mode was significantly greater than in subjects receiving sham-mode in the whole sample [NIR (n=9) −2.55±1.88 vs. sham (n=11) −0.45±1.21; z=2.548, p=0.011)] and in the completers [NIR (n=5) −3.4±1.95 vs. sham (n=7) −0.14±1.21; z=2.576, p=0.010)]. FIGS. 3 and 4 illustrate the mean SAFTEE sex total scores over the course of the study for the two t-PBM groups (NIR and sham), in the whole sample and in completers. After removing two subjects from the analyses—due to lack of post-treatment assessments—findings were confirmed [NIR (n=9) −2.55±1.88 vs. sham (n=9) −0.55±1.33; z=2.215, p=0.027)]. When splitting the overall sample based on gender, significance for the same comparison was reached in women [NIR (n=5) −3.0±2.24 vs. sham (n=6) −0.3±0.82; z=2.196, p=0.028)] but not in the smaller sample of men [NIR (n=4) −2.0±1.41 vs. sham (n=5) −0.6±1.67; z=1.014, p=0.310)], see FIGS. 5 and 6.

The effect sizes for the improvement in overall sexual functioning were d=1.33 (n=20) and d=1.23 (n=18) (Cohen's d). These effects were 55% and 73% greater than the ones observed for the decrease in severity of depression [d=0.86 (n=20) and d=0.71 (n=18)]. A significant decrease in the overall sexual dysfunction, but not in the depression severity, was documented as early as at completion of week 2 in the overall sample [NIR (n=9) −1.11±1.17 vs. sham (n=11) −0.09±1.05; z=1.972, p=0.049)]. A significant decrease in the overall sexual dysfunction, but not in the depression severity, was also documented after completion of week 3, when removing two subjects with lack of post-treatment assessments [NIR (n=9) −2.11±1.45 vs. sham (n=9) −0.44±1.24; z=2.313, p=0.021)]. The decrease in severity of depression was not significant in both samples, at any time point, (n=20 and n=18; of note both samples were less than the original ELATED-2 sample of n=21, as previously reported).

Impaired Libido

Figure 7:
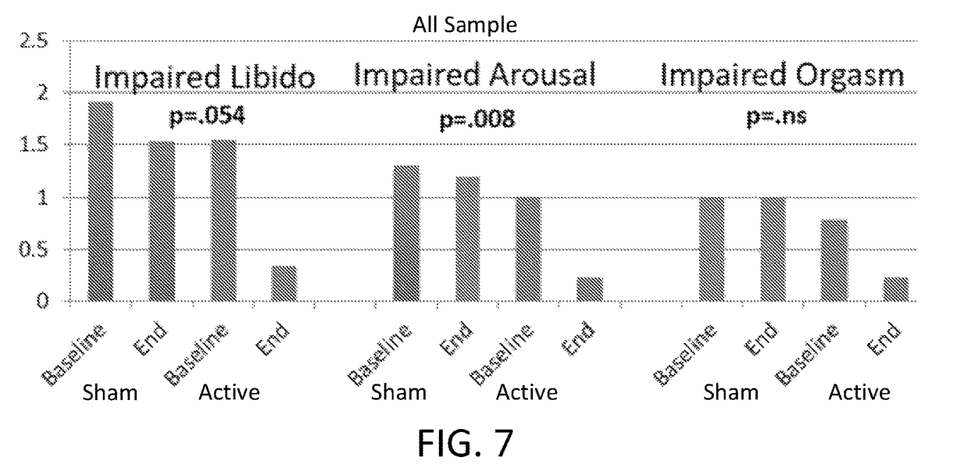
FIG. 7 is a chart of Item Scores of Impaired Libido, Impaired Arousal, and Impaired Orgasm pre-treatment and post treatment for all sample.
Figure 8:
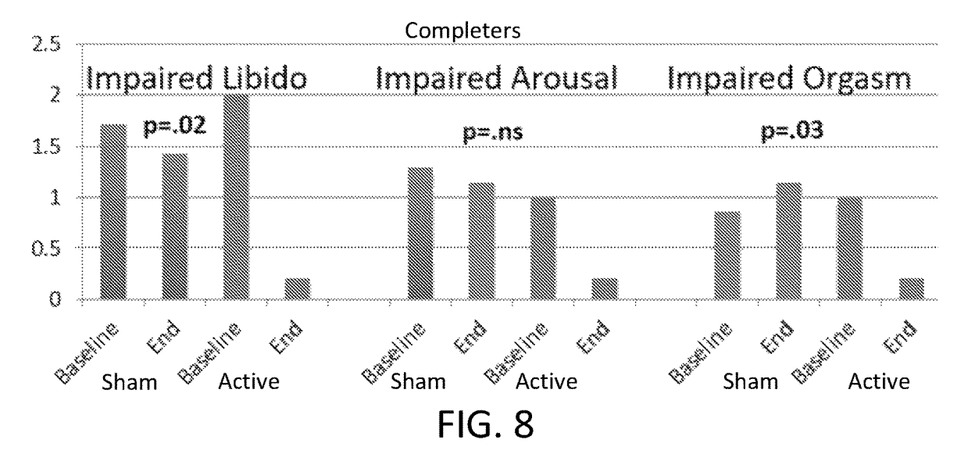
FIG. 8 is a chart of Item Scores of Impaired Libido, Impaired Arousal, and Impaired Orgasm pre-treatment and post treatment for completers.

The comparison of the mean change in SAFTEE item 36 score "loss of sexual interest" approached significance in the whole sample [NIR (n=9) −1.2±1.09 vs. sham (n=1) −0.4±0.67; z=1.930, p=0.054)] and was significant in the completers [NIR (n=5) −1.8±1.09 vs. sham (n=7) −0.3±0.49; z=2.276, p=0.023)]. The percent decrease in severity of "loss of sexual interest" in the t-PBM NIR group was −79% and −90%, respectively in the whole sample and in completers, see FIGS. 7 and 8.

Impaired Sexual Arousal

The comparison of the mean change in SAFTEE item 37 "problems with sexual arousal (erection or lubrication)" reached significance in the whole sample [NIR (n=9) −0.8±0.67 vs. sham (n=11) −0.1±0.30; z=2.633, p<0.001)] but failed to in the completers [NIR (n=5) −0.8±0.84 vs. sham (n=7) −0.1±0.38; z=1.659, p=0.097)]. The percent decrease in severity of "problems with sexual arousal" in the t-PBM NIR group was −78% and −80%, respectively in the whole sample and in completers.

Delayed or Absent Orgasm

The comparison of the mean change in SAFTEE item 38 "delayed or absent orgasm" was significant in completers [NIR (n=09) −0.6±0.73 vs. sham (n=11) 0.0±0.89; z=1.738, p=0.08); NIR (n=5) −0.8±0.84 vs. sham (n=7) −0.3±0.76; z=2.228, p=0.026)]. The percent decrease in severity of "delayed or absent orgasm" in the t-PBM NIR group was −72% and −80%, respectively in the whole sample and in completers.

DISCUSSION

This study on the effects of t-PBM on sexual dysfunction demonstrated a significant therapeutic effect, with reversal of sexual dysfunction in patients with multifactorial causation.

Three of the study subjects reported improvement in sexual function, which were unusual in terms of magnitude and fast onset. The three clinical cases—briefly reported in the examples below—led to the exploratory analyses described here to test a putative effect of t-PBM on sexual functioning in the overall sample. We relied on the use of a composite score, the SAFTEE sex total score, to describe the sexual impairment. The SAFTEE scale had been included in the protocol to measure potential new-onset side effects related to t-PBM; in this context, we used the SAFTEE scale to track the overtime change in sexual functioning, the latter was impaired on average in this cohort of MDD patients.

The unanticipated finding that t-PBM improved sexual function in our cohort of depressed subjects was documented in the whole sample and in the completers' sample. The finding was still significant in the subsample of women, but not in the reduced sample of men. Interestingly, while there were fewer men than women in the study, the magnitude of the decrease in severity of sexual dysfunction was similar across genders—and in fact slightly higher in men (−75% in women and −80% in men)—when receiving t-PBM. It is prudent to assume a relationship between the lack of statistically significant findings in men and the lack of power.

Dimensions of sexual dysfunction were tested to elucidate which were most likely to drive the overall study findings. In the whole sample, sexual arousal improved significantly more with t-PBM than sham; and in completers both libido and orgasm improved significantly more with t-PBM, but not arousal. It is striking that similar decreases in severity of sexual dysfunction occur across dimensions after exploring the magnitude of the improvements in each sexual dimension. Therefore, interpretation led to the lack of statistical significance of some of the comparisons as likely related to lack of power; in fact, the measure for each dimension of sexual dysfunction might have low sensitivity due to the four point Likert scale (score range 0-3). The magnitude of decrease in severity for each sexual dimension appeared slightly greater in completers (impaired libido −90%; impaired arousal and impaired orgasm −80%), compared to the whole sample (impaired libido −79%; impaired arousal −78%; impaired orgasm −72%). Completers might have benefited from more treatment sessions and from longer exposure time to t-PBM, since exposure increased from 20 min to 30 min over the course of the study.

The nature or cause of the sexual dysfunction in our cohort is multifactorial; while the underlying depressive syndrome was common to all included patients; multiple other potential factors coexisted such as comorbid medical conditions and pharmacotherapies. Given previous demonstration showed an antidepressant effect for t-PBM in the same cohort—studies conducted to the effect of t-PBM on sexual dysfunction from its effect on depression occurred. In the current study, the timing and the magnitude of the effect of t-PBM on sexual dysfunction were much faster and far greater than its effect on depression; this contradicts any speculation that sexual function improved because of the lessening of the depressive syndrome. On the contrary, t-PBM is likely to benefit sexual function independently from the outcome of depression.

T-PBM effects sexual function in a number of ways. At least two non-limiting hypotheses about mechanisms for t-PBM effects on sexual functions can follow. First, direct neuromodulation mediates the effect of the central nervous system, more specifically of the targeted prefrontal cortex (i.e. enhanced EEG activity). Second, an increase in signaling molecules mediates the effect, such as neuronal nitric oxide (NO). Not only NO is increased by t-PBM with NIR, but also neuronal, intra- or extra-cellular NO in the hypothalamus is postulated to be essential to onset of puberty and to fertility, and regulates GnRH and LH release.

A clinical observation drove this study, at least in part, and therefore tested an informed hypothesis. During the conduct of the clinical trial, neither investigators nor study subjects expected an effect of t-PBM on sexual functioning; this might have increased our chance to detect a signal by decreasing the placebo effect.

EXAMPLES

The following examples provide case vignettes from the study cohort.

Example 1

A 65-year-old, divorced retired man, father of two grown-up children. At the time of the study, he was in a romantic relationship but lived independently. At baseline, he rated his loss of sexual interest as "severe" and his problems with sexual arousal (erection) as "moderate". After two t-PBM sessions (one week), the patient reported only "mild" loss of sexual interest and "mild" problems with sexual arousal. Despite some waxing and waning of his ratings on sexual functioning from week to week, after completion of fifteen t-PBM sessions the patient consistently reported no problems with erection and only minimal decrease in sexual interest. During study visits, the patient joked that he had been more sexually active with his girlfriend to the point that she had asked him to return to his own apartment and spend the following nights there.

Example 2

A 44 year-old, married woman; a professional and mother of two young children. Before entering the study she had been treated for depression with Venlafaxine 75 mg every day for six weeks and continued this medication during the study. While she did not experience pronounced impairment with her sexual function before starting her antidepressant medication (despite being depressed), she then complained of both decreased libido and anorgasmia on Venlafaxine. Before starting her t-PBM sessions, she rated her loss of sexual interest as "severe", her problems with sexual arousal "mild" and her delayed or absent orgasm as "moderate". After the first two sessions (1 week) her loss of sexual interest was rated as "moderate", her issues with lubrication resolved and her delayed or absent orgasm was "mild". After ten t-PBM sessions her sexual dysfunction had completely resolved. At the end of the study, the patient was perplexed that t-PBM was not a popular intervention and she equated her sexual functioning to her adolescence.

Example 3

A 27 year-old single man, in a romantic relationship. At baseline, he reported "mild" loss of sexual interest and problems with sexual arousal (erection). At week 1 both sexual interest and arousal were normal and at week 2 only loss of sexual interest was present and rated as "mild". During the study (week 1) the patient reported that his sexual interest and activity had nearly doubled: he went from having sex 4-5 times per week to 8-9 per week. After four t-PBM sessions (2 weeks) the patient stopped coming to the study visits and eventually dropped from the study.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. A device configured for treating a sexual dysfunction of a subject, the device comprising:
a power source;
a light source configured to receive power from the power source to cause the light source to emit near-infrared light;
a processor; and
a housing configured to position the light source to deliver the near-infrared light to a region of interest of the subject via transcranial photobiomodulation, the near-infrared light being in a dosimetry and duration sufficient to treat the sexual dysfunction of the subject,
wherein the sexual dysfunction includes at least one of impaired libido, impaired sexual arousal, delayed orgasm, or absent orgasm, and
wherein the near-infrared light is delivered at a wavelength of 830 nm at an average irradiance up to 36.2 mW/cm2 and a fluence over 30 min up to 65.2 J/cm2, with a treatment window of 28.7 cm2.

2. The device of claim 1, wherein the subject is depressed, and wherein the near-infrared light delivered to the subject is configured to treat the sexual dysfunction of the subject independently of treating the depression of the subject.

3. The device of claim 1, wherein the processor is configured to cause the light source to implement a duration of delivery of near infrared light of about 1 minute to about 120 minutes per day.

4. A method of controlling a device configured for treating sexual dysfunction of a subject, the method comprising:
providing power to a device having a light source to cause the light source to emit near-infrared light to a region of interest of the subject; and
delivering the near-infrared light to a region of interest of the subject via transcranial photobiomodulation, the near-infrared light being in a dosimetry and duration sufficient to treat the sexual dysfunction, and
wherein the sexual dysfunction includes at least one of impaired libido, impaired sexual arousal, delayed orgasm, or absent orgasm, and
wherein the near-infrared light is delivered at a wavelength of 830 nm at an average irradiance up to 36.2 mW/cm2 and a fluence over 30 min up to 65.2 J/cm2, with a treatment window of 28.7 cm2.

5. The method of claim 4, wherein the duration of delivery of the near-infrared light is about 1 minute to about 120 minutes per day.

6. A device configured for treating sexual dysfunction of a subject, the device comprising:

a power source;

a light source configured to receive power from the power source to cause the light source to emit near-infrared light, wherein the near-infrared light has a wavelength of about 830 nm;

a processor; and a housing configured to position the light source to deliver the near-infrared light to a region of interest of the subject via transcranial photobiomodulation, the near-infrared light being in a dosimetry and duration sufficient to treat the sexual dysfunction, wherein the sexual dysfunction of the subject includes at least one of impaired libido, impaired sexual arousal, delayed orgasm, or absent orgasm, and wherein the near-infrared light is delivered at a wavelength of 830 nm at an average irradiance up to 36.2 mW/cm2 and a fluence over 30 min up to 65.2 J/cm2, with a treatment window of 28.7 cm2.

7. The device of claim 6, wherein the duration of delivery of the near-infrared light is about 1 minute to about 120 minutes per day.

8. The device of claim 1, wherein the sexual dysfunction of the subject is a first disorder of the subject, wherein the subject has a second disorder, and wherein the near-infrared light that is delivered to the subject via transcranial photobiomodulation is configured to cause a decrease in the severity of the sexual dysfunction, but not cause a decrease in the severity of the second disorder.

9. The device of claim 8, wherein the second disorder is depression.

10. The device of claim 6, wherein the transcranial photobiomodulation is administered bilaterally to the subject, and wherein the transcranial photobiomodulation is administered bilaterally to a forehead of the subject.

11. The method of claim 4, wherein the subject is depressed, and wherein the near-infrared light delivered to the subject via transcranial photobiomodulation is configured to treat the sexual dysfunction independently of the depression of the subject.

12. The device of claim 1, wherein the near-infrared light is configured to treat the sexual dysfunction of the subject, with the subject not being depressed.

13. The method of claim 4, wherein the subject is not depressed.

14. The device of claim 6, wherein the near-infrared light is configured to treat the sexual dysfunction of the subject, with the subject not being depressed.

15. The device of claim 1, wherein the transcranial photobiomodulation is administered bilaterally to the subject, and wherein the transcranial photobiomodulation is administered bilaterally to a forehead of the subject.

16. The device of claim 4, wherein the transcranial photobiomodulation is administered bilaterally to the subject, and wherein the transcranial photobiomodulation is administered bilaterally to a forehead of the subject.

* * * * *

UNITED STATES PATENT AND TRADEMARK OFFICE
CERTIFICATE OF CORRECTION

PATENT NO. : 11,577,094 B2
APPLICATION NO. : 16/500775
DATED : February 14, 2023
INVENTOR(S) : Paolo Cassano It is certified that error appears in the above-identified patent and that said Letters Patent is hereby corrected as shown below:

In the Specification

Column 9, Line 35, "(n=1)" should be --(n=11)--.

Signed and Sealed this
Twenty-second Day of August, 2023

Katherine Kelly Vidal
*Director of the United States Patent and Trademark Office*